US007688071B2

(12) United States Patent
Cheng et al.

(10) Patent No.: US 7,688,071 B2
(45) Date of Patent: Mar. 30, 2010

(54) NMR MEASUREMENT OF WAX APPEARANCE IN FLUIDS (75) Inventors: Yuesheng Cheng, Edmonton (CA); Abdel M. Kharrat, Edmonton (CA)

(73) Assignee: Schlumberger Technology Corporation, Sugar Land, TX (US)

(*) Notice: Subject to any disclaimer, the term of this patent is extended or adjusted under 35 U.S.C. 154(b) by 151 days.

(21) Appl. No.: 11/872,906

(22) Filed: Oct. 16, 2007

(65) Prior Publication Data
US 2009/0066330 A1 Mar. 12, 2009

Related U.S. Application Data (60) Provisional application No. 60/898,505, filed on Jan. 31, 2007.

(51) Int. Cl.
G01V 3/00 (2006.01)
(52) U.S. Cl. ............... 324/321; 324/318; 324/315; 324/307; 324/306; 324/303
(58) Field of Classification Search ......... 324/300–322, 324/336–343; 600/407–435
See application file for complete search history.

(56) References Cited

U.S. PATENT DOCUMENTS

| | | | | |
|---|---|---|---|---|
| 3,153,756 A * | 10/1964 | Williams et al. | | 324/310 |
| 3,987,361 A * | 10/1976 | Martin et al. | | 324/315 |
| 4,860,581 A | 8/1989 | Zimmerman et al. | | |
| 6,140,817 A | 10/2000 | Flaum et al. | | |
| 6,315,981 B1 * | 11/2001 | Unger | | 424/9.323 |
| 6,346,813 B1 * | 2/2002 | Kleinberg | | 324/303 |
| 6,825,657 B2 * | 11/2004 | Kleinberg et al. | | 324/303 |
| 6,841,996 B2 * | 1/2005 | Madio et al. | | 324/303 |
| 6,859,032 B2 | 2/2005 | Heaton et al. | | |
| 7,053,611 B2 | 5/2006 | Freedman | | |
| 7,126,332 B2 * | 10/2006 | Blanz et al. | | 324/303 |
| 7,205,762 B2 * | 4/2007 | Blanz et al. | | 324/303 |
| 7,253,618 B1 | 8/2007 | Freedman et al. | | |
| 7,368,909 B2 * | 5/2008 | Blanz et al. | | 324/303 |
| 7,486,071 B2 * | 2/2009 | Care et al. | | 324/306 |
| 7,489,132 B2 * | 2/2009 | Arik et al. | | 324/318 |
| 2003/0006768 A1 * | 1/2003 | Kleinberg et al. | | 324/303 |
| 2004/0119471 A1 * | 6/2004 | Blanz et al. | | 324/303 |
| 2004/0140800 A1 * | 7/2004 | Madio et al. | | 324/303 |
| 2005/0024053 A1 * | 2/2005 | Care et al. | | 324/309 |
| 2006/0192554 A1 * | 8/2006 | Blanz et al. | | 324/303 |
| 2007/0182408 A1 * | 8/2007 | Blanz et al. | | 324/303 |
| 2009/0066330 A1 * | 3/2009 | Cheng et al. | | 324/315 |

* cited by examiner

*Primary Examiner*—Brij B. Shrivastav
*Assistant Examiner*—Tiffany A Fetzner
(74) *Attorney, Agent, or Firm*—T. Chyau Liang; Wayne I. Kanak (57) ABSTRACT

A method for determining a wax appearance temperature of a fluid includes obtaining nuclear magnetic resonance (NMR) measurements of the fluid at a plurality of temperatures; deriving a NMR parameter from each of the NMR measurements; and determining the wax appearance temperature by analyzing the NMR parameter as a function of temperature. An apparatus for detecting wax appearance in a fluid includes a sample cell for holding a fluid for nuclear magnetic resonance (NMR) measurements at a plurality of temperatures; a temperature measuring device disposed proximate the sample cell; a magnet for polarizing molecules in the fluid in the sample cell; at least one radiofrequency (RF) coil for generating pulses of magnetic field and for detecting NMR signals; and circuitry for controlling and measuring the temperature of the fluid in the sample cell and for obtaining NMR measurements.

10 Claims, 9 Drawing Sheets
(3 of 9 Drawing Sheet(s) Filed in Color)

NMR MEASUREMENT OF WAX APPEARANCE IN FLUIDS

CROSS REFERENCE TO RELATED APPLICATIONS

This application claims priority from U.S. Provisional Patent Application 60/898,505, filed on Jan. 31, 2007, which is incorporated by reference herein in its entirety.

BACKGROUND OF INVENTION

1. Field of the Invention

The invention relates generally to compositional characterization and quantification of solid deposits from hydrocarbon fluids.

2. Description of Related Art

When fluids are transported by flowing through pipes or tubing, the deposition of solids from the fluid onto the interior walls of the pipes or tubing may impair fluid flow. An example of such fluids is crude oil. Some solids may be pre-existing in the fluids, and some solids may form during storage or transport due to environmental changes that lead to phase transition. Crude oils from many formations commonly contain solids, often as one or more of waxes (paraffin waxes), asphaltenes, sulfur, scale, and hydrates. Paraffin waxes are essentially mixtures of long-chain n-paraffins with carbon chain lengths ranging from $C_{15}$ to $C_{90}+$.

Asphaltenes and residual oil components often co-precipitate with the paraffin waxes and result in varying appearance (color) and texture of the precipitated solids. Asphaltenes are generally compounds including more than about 70 carbon atoms, which are mostly aromatic polycyclic compounds variably substituted with alkyl groups. Asphaltenes may also contain heteroatoms (such as nitrogen, sulfur, or oxygen), metals (such as nickel, vanadium, or iron), or both. Hydrates generally include water molecules in an ice-like structure encaging one or more organic compounds. The organic compounds encaged by the ice-like structure are commonly methane, ethane, propane, or other alkanes with less than about 10 carbon atoms.

Under many conditions, the compounds that are capable of forming solids in a fluid may remain dissolved in the fluid. However, when a fluid, such as crude oil, is transported via pipe, such as from a geologic formation to a wellhead via production tubing or from a wellhead or a storage vessel to a refinery via a pipeline, changes in the pressure, temperature, composition, or other parameters of the flowing fluid may lead to precipitation and deposition of solids. Deposition in a pipe is generally undesirable, because deposited solids would at least partially block the pipe, leading to reductions in the flow rates of fluids in the pipe. When this occurs, expensive and time-consuming cleaning of the pipe is required to restore the maximum flow rates of the fluids.

Similar problems can also arise for other fluids which may contain solids. Such fluids, either liquids or gases, include fluids used in the industrial production of paint, food products, pharmaceuticals, plastics, and paper and paper products, among other industries.

Currently, a visual pressure-volume-temperature (PVT) cell equipped with fiber optic light transmission probes (source and detector) is typically used to detect the onset of organic solids precipitation (due to temperature, pressure and/or compositional changes) concurrently with fluid volumetric measurements. These fiber optic probes are mounted across the windows of the visual PVT cell. The visual PVT cell together with the optical probes and the computerized pump are referred to as a Solids Detection System (SDS). The measurement principle of the SDS is based on transmittance of a laser light through the test fluid white temperature, pressure, or the fluid composition is being changed.

The entire system is typically controlled by a software package that accomplishes two significant objectives. First, a computerized pump is used to control and maintain the system pressure during isobaric temperature sweeps for wax precipitation experiments. Second, the software (in real time) records and displays the system temperature, pressure, solvent volume, time, and, most importantly, the power of transmitted light (PTL) through the test fluid.

The standard SDS configuration discussed above may be further improved with the addition of high-pressure microscopy (HPM) in series. The HPM cell is a small sapphire prototype with variable internal diameters (and hence working volumes) It is typically connected to the bottom of a PVT cell inside the same air-bath oven.

Another common method for measuring wax appearance temperature and wax disappearance temperature uses cross polar microscopy (CPM). CPM is based on the fact that most crystalline materials rotate the plane of polarization of transmitted polarized light. By crossing two prisms on opposite sides of the oil sample, all light is initially blocked and the entire field of view appears black. On cooling, the crystallizing material appears as bright spots against this black background. This technique usually provides a conservative (or highest) value of the crude oil cloud point temperature due to CPM's ability to detect small crystals, i.e. during early stages of wax crystallization.

While such prior art methods, such as SDS and CPM, have been found to be useful, their sensitivities may not be sufficient for some applications. With these prior art methods, only particles larger than 2 microns are typically detected. This limitation results in a delay in the measurements of wax formation. As a result, there is often a discrepancy between the wax appearance temperature and the wax disappearance temperature. Consequently, there still exists a need for better methods for wax appearance temperature measurements.

BRIEF SUMMARY OF THE INVENTION

Embodiments of the invention rely on the behavior chance of the wax molecules when detected by nuclear magnetic resonance (NMR), particularly low-field NMR. The NMR parameters, such as relaxation times ($T_1$ and $T_2$) and self-diffusion (D), are linked to the chemical and physical properties of the sample. Thus, the changes in the NMR parameters can be detected at the molecular level and used to infer the property changes of the sample.

Methods of the invention can be used to detect wax molecules with better sensitivity than SDS or CPM. The NMR relaxation times are described in terms of correlation functions and spectral densities. Thus, the NMR relaxation times involve a large number of molecules and, therefore, the NMR methods operate on the mesoscopic space scale between 1 nm and 0.1 µm. Furthermore, the NMR methods in accordance with embodiments of the invention may be used downhole under reservoir conditions, which can provide more meaningful results than methods based on laboratory devices.

In another aspect, the present invention relates to methods for determining a wax appearance temperature of a fluid. A method in accordance with one embodiment of the invention includes obtaining NMR measurements of the fluid at a plurality of temperatures; deriving a NMR parameter from each of the NMR measurements; and determining the wax appearance temperature by analyzing the NMR parameter as a function of temperature.

In one aspect, the present invention relates to apparatus for detecting wax appearance in a fluid. An apparatus in accordance with one embodiment of the invention includes a sample cell for holding a fluid for NMR measurements at a plurality of temperatures; a temperature measuring device disposed proximate the sample cell; a magnet for polarizing molecules in the fluid in the sample cell; at least one radiofrequency (RF) coil for generating pulses of magnetic field and for detecting NMR signals; and circuitry for controlling and measuring the temperature of the fluid in the sample cell and for obtaining NMR measurements.

Other aspects and advantages of the invention will be apparent from the following description and the appended claims.

BRIEF DESCRIPTION OF DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Embodiments of the invention relate to methods and apparatus for measuring wax appearance temperature for a fluid, such as live oil samples, using nuclear magnetic resonance (NMR). The wax appearance temperature is the temperature at which wax or wax-like materials begins to appear in a fluid upon cooling. This temperature is substantially the same as the temperature at which the wax begins to disappear when a mixture containing wax or wax-like materials is heated. Therefore, "wax appearance" temperatures are used in a broad sense to include wax disappearance temperatures. The currently used methods typically use microscopy or some visual means to detect wax formation white the sample is cooled. Methods in accordance with embodiments of the present invention detect phase changes using a NMR device that detects changes in behavior at the molecular level. Therefore, embodiments of the invention are typically more sensitive than prior art methods.

NMR tools are among the common tools used in the oilfield. The signals measured by NMR logging tools arise from the selected nuclei present in the probed volume. Because hydrogen nuclei are the most abundant and easily detectable, most NMR logging tools are tuned to detect hydrogen resonance signals (from either water or hydrocarbons). These hydrogen nuclei have different dynamic properties (e.g., diffusion rate and tumbling/rotation rate) that are dependent on their environments, such as the chemical structure and size of the molecules in which they reside. The different dynamic properties of these nuclei manifest themselves in different nuclear spin relaxation times (i.e., spin-lattice relaxation time ($T_1$) and spin-spin relaxation time ($T_2$); spin-lattice relaxation is also referred to as longitudinal relaxation, and spin-spin relaxation as transverse relaxation). For example, molecules in viscous oils cannot diffuse or tumble as fast as those in light oils. As a result, they have relatively short relaxation times. Similarly, molecules in solids (or wax) are not free to tumble or diffuse, and, therefore, molecules in solids will have extremely short relaxation times. These observations suggest that NMR data (e.g., relaxation times) can provide information on molecular properties of hydrocarbons in fluid samples.

NMR devices may be incorporated into various downhole tools, such as the Modular Formation Dynamics Tester (MDT) tool from Schlumberger Technology Corporation of Sugar Land, Tex., USA. The MDT tool may be used to test fluid properties or obtain formation fluid samples from the formation. The MDT tool may be suspended by a wireline and then lowered into the borehole of a well. The instrument is secured to the walls of the borehole and samples of the formation fluid are extracted. Such a tool is described in U.S. Pat. No. 4,860,581, which is incorporated herein by reference in its entirety.

Figure 1:
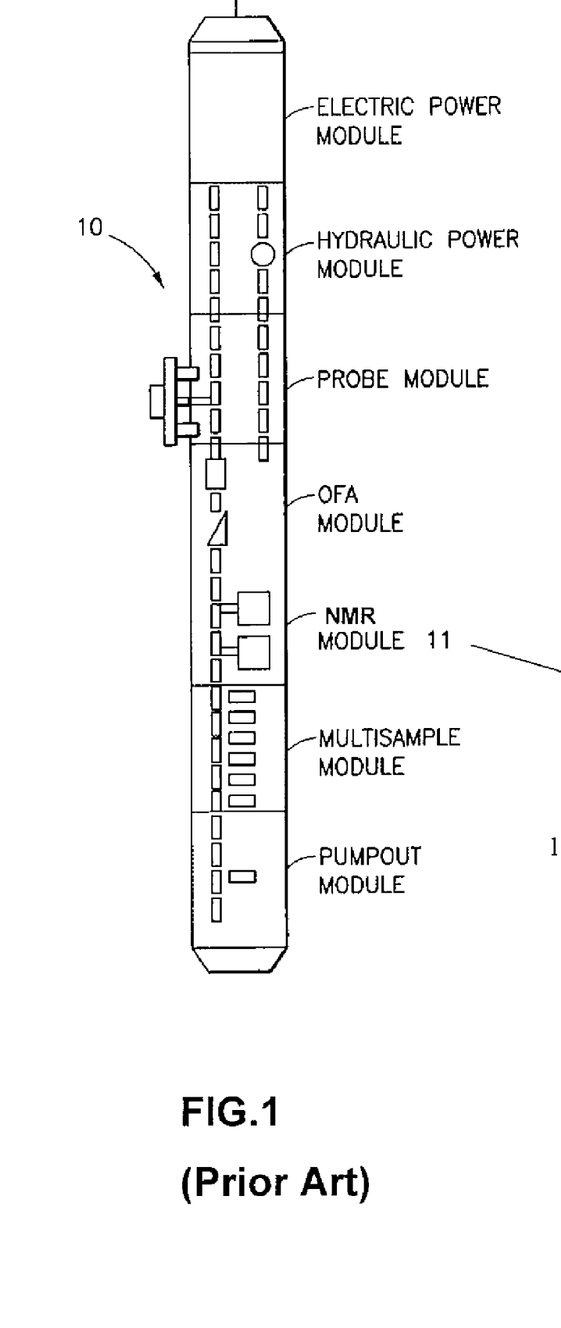
FIG. 1 shows a downhole tool that includes an NMR module in accordance with one embodiment of the invention.

FIG. 1 illustrates a downhole tool 10, such as an MDT tool, for use in a wellbore. The downhole tool 10 shown in FIG. 1 has various modules therein, including an NMR module 11. In general, tools that extract fluids from formations are called "sampling tools." Most sampling tools pump formation fluids for a substantial period of time in order to minimize contamination by mud filtrate. The MDT tool 10 has a pumpout module for this purpose. During the pumping process, fluid properties are measured by various means, such as low-frequency electrical conductivity, dielectric constant, and/or optical properties. In the initial stage, this fluid is discarded by being pumped either into the borehole or back into the formation at a remote point. When the sensors show the fluid is substantially free of contaminants, the fluid is redirected to one or more sample bottles in the multisample module. Subsequently, the fluid is transported in such bottles to the surface for extensive examination and testing. In addition, measurements of bubble point can be made inside the tool downhole.

Fluid sampling tools comprise a pumpout module that can be used, for example, to draw fluids from the formation, circulate them through the instrument for analysis, and then expel these fluids to the borehole. The MDT tool can also retain samples of formation fluids in sample bottles, which are then transported to the surface. The samples are transferred at the surface from the sample bottles to transportation bottles. The formation fluid samples are then sent to pressure-volume-temperature laboratories (PVT labs) for analysis of their composition and their physical properties. Conventional PVT labs provide a broad range of measurements and services. These fluid samples may also be analyzed for wax appearance temperatures in the laboratories using NMR in accordance with embodiments of the invention.

Figure 1A:
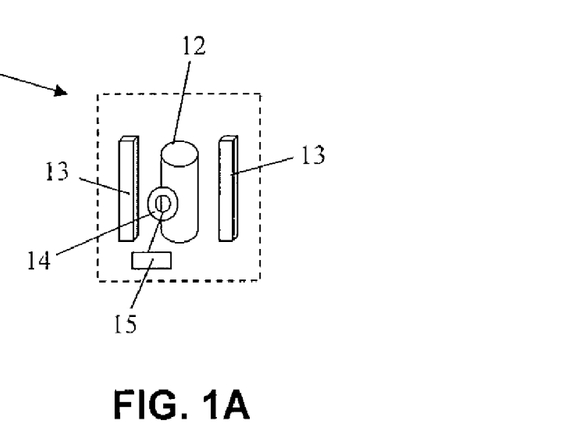
FIG. 1A shows an example of an NMR module in accordance with one embodiment of the invention.

In accordance with some embodiments of the invention, the fluids drawn into the downhole tool may be analyzed with the NMR module 11 under downhole conditions. FIG. 1A shows a schematic illustrating an NMR module. As shown in FIG. 1A, the NMR module 11 includes a sample cell 12 disposed between a pair of permanent magnets 13. A fluid sample held in the sample cell 12 will be polarized by the static magnetic field of the permanent magnets 13. The NMR module 11 also includes a coil 14 (a radiofrequency antenna) that may be used to generate pulses of magnetic fields for the measurement of NMR signals. In addition, coil 14 (or another similar coil) may be used to detect the NMR signals, e.g., spin echoes from the nuclei. Coil 14 is connected to circuitry 15, which is used to control the pulsing of the magnetic fields and receive/record the detected signals. The circuitry may be disposed in the NMR module or at a remote location on the downhole tool.

The operation of NMR instruments is well known to one skilled in the art and further details may be found in related literature or patents, including U.S. Pat. Nos. 6,140,817 and 6,859,032, which are incorporated herein by reference in their entireties.

Several NMR parameters may be measured that can be used to probe fluid properties, including the wax appearance temperature. Most NMR measurements are designed to measure spin-lattice (longitudinal) relaxation times ($T_1$) and/or spin-spin (transverse) relaxation times ($T_2$), typically of hydrogen nuclei. In addition, some NMR measurements may be designed to provide a ratio of $T_1/T_2$ from $T_1$-$T_2$ two-dimensional measurements, while other NMR measurements may be designed to provide diffusion constants (D). Any suitable NMR parameters (e.g., $T_1$, $T_2$, $T_1/T_2$, and/or D) may be used with embodiments of the present invention, though the following discussion uses $T_1$ and $T_2$ relaxation times to illustrate embodiments of the present invention.

Figure 2:
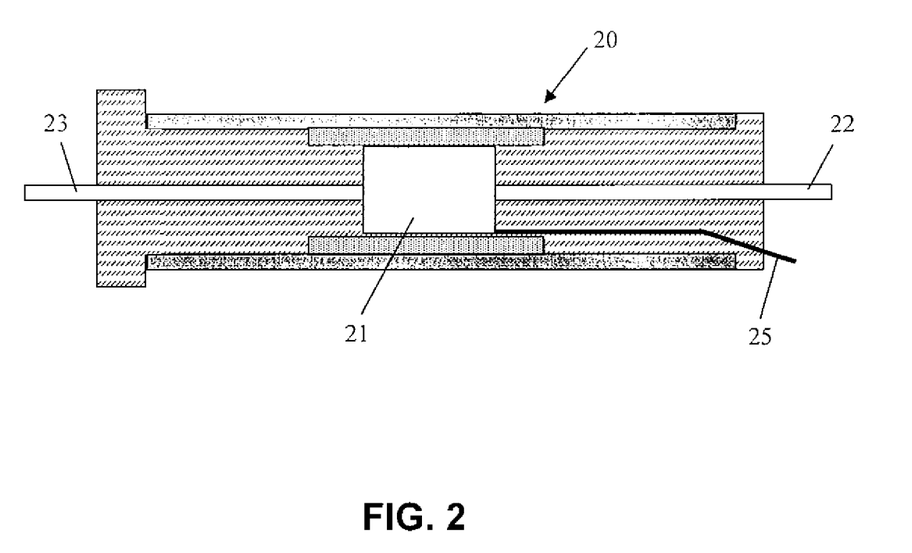
FIG. 2 shows an NMR sample cell in accordance with one embodiment of the invention.

FIG. 2 illustrates an example of an NMR sample cell 20 in accordance with one embodiment of the invention. The sample cell 20 includes a sample holder (sample chamber) 21 for holding a fluid sample while taking NMR measurements. The sample may be charged under reservoir conditions into the sample holder 21. The NMR measurement may be performed using any suitable NMR instrument, such as a low-field NMR instrument or an NMR logging tool. In addition, the sample cell 20 may include an inlet 22 and an outlet 23 for charging the fluids in the sample holder 21 or for use in measuring a fluid flowing through the sample holder 21. The sample holder 21 may also include a thermocouple 25 or a similar temperature measuring device for accurately determining the temperatures of the fluid samples in the sample holder 21. The temperature determination may be controlled by circuitry, such as that shown as 15 in FIG. 1A. The sample cell 20 may be adapted for use in a laboratory NMR instrument, on a pipeline, or in an NMR module of a downhole tool.

Any NMR measurement technique known in the art may be used. For example, for the measurements of $T_2$ relaxation, a typical CPMG pulse sequence (or any similar pulse sequence) is often used. In addition, the pre-pulse delay times and/or the inter-echo delay times in a CPMG pulse train may be varied to obtain other NMR properties, including the $T_1$ relaxation and diffusion constants (D). All these techniques can be found in general NMR texts and relevant patents, such as those mentioned above. In addition, pulsed field gradients may be used to facilitate the measurements of certain NMR parameters (e.g., diffusion constants, D). Examples of gradient NMR measurements, for example, may be found in U.S. Pat. No. 7,053,611, which is incorporated herein by reference in its entirety.

The NMR measurement data are then analyzed to derive the desired parameters. For example, the parameters collected from such NMR measurements may include $T_1$, $T_2$, $T_1/T_2$, and/or diffusion (D).

As noted above, these NMR parameters are functions of the molecular dynamics of the components in the fluids. For example, upon temperature changes, some components in the fluids may start to form wax (or precipitate); such physical state changes will result in altered NMR dynamic parameters ($T_1$, $T_2$, $T_1/T_2$, and/or D). Specifically, when wax starts to appear in a fluid (i.e., during the phase transition), a particular molecule may come in and out of the wax. That is, in dynamic equilibrium between liquid and solid states. As a result of such equilibrium, the molecular dynamics will appear as an average of a fluid state and the solid state in the NMR measurements. Because the relaxation times of solids are significantly shorter than those of the fluids, the "apparent" relaxation time during this phase-transition period will be significantly reduced, as compared with the fluid state. Similarly, the diffusion will also be significantly reduced. Therefore, wax appearance in a fluid may be detected by chances of the NMR parameters.

Relaxation of nuclear magnetization commonly arises from magnetic dipolar coupling between nuclei. In a fluid-like system, molecular diffusion and reorientation produce magnetic fields. Nuclear magnetic relaxation times ($T_1$ and $T_2$), which reflect the efficiency of the local interactions, are given as:

$$\frac{1}{T_1} = \frac{3\gamma^4\eta^2}{10r^6}\left[\frac{\tau_c}{1+\omega_0^2\tau_c^2} + \frac{4\tau_c}{1+4\omega_0^2\tau_c^2}\right] \quad (1)$$

$$\frac{1}{T_2} = \frac{3\gamma^4\eta^2}{20r^6}\left[3\tau_c + \frac{5\tau_c}{1+\omega_0^2\tau_c^2} + \frac{2\tau_c}{1+4\omega_0^2\tau_c^2}\right] \quad (2)$$

where $\tau_c$ is the correlation time of the molecular tumbling motion.

$$\text{For } \omega\tau \ll 1, \quad \frac{1}{T_1} = \frac{1}{T_2} = \frac{3\gamma^4\eta^2}{10r^6}[5\tau_c]. \quad (3)$$

$$\text{For } \omega\tau \gg 1, \quad \frac{1}{T_1} = \frac{3\gamma^4\eta^2}{10r^6}\left[\frac{2}{\omega_0^2\tau_c}\right] \quad (4)$$

and $$\frac{1}{T_2} = \frac{3\gamma^4\eta^2}{20r^6}[3\tau_c]. \quad (5)$$

In general, the correlation time, $\tau_c$, for non-viscous liquid is very short. With water, for instance, $\tau_c$ is about $10^{-12}$ seconds. On the other hand, $\tau_c$, for solids is very long, about $10^{-5}$ seconds.

It is assumed that the re-orientation mechanisms are thermally activated. The temperature dependence of the correlation time $\tau_c$ is a function of the molecular dynamics of the system. Their relationship can be described by Arrhenius equation:

$$\tau_c = \tau_0 e^{E_a/RT} \quad (6)$$

where $E_a$ is the activation energy of the re-orientation process, R is the gas constant, and $\tau_0$ is a constant.

When a sample comprises of a mixture of different components, these components may have different $T_1$ or $T_2$ values. As a result, the NMR results often show a distribution of $T_1$ or $T_2$ values. These $T_1$ or $T_2$ values may be analyzed as such. However, it is often more convenient to analyze such $T_1$ or $T_2$ distribution as a mean (or average) of the values. In particular, it has been found that logarithmic means of $T_1$ or $T_2$ distributions are good indicators of properties of the mixtures. The logarithmic mean (LM) of $T_1$ or $T_2$ distributions may be calculated in a similar fashion, as illustrated below using $T_1$ as an example:

$$T_{1LM} = \left( \prod_{i=1}^{n} T_{1i}^{n_i} \right)^{\frac{1}{\sum_i n_i}}, \text{ or} \quad (7)$$

$$\ln(T_{1LM}) = \frac{\sum_i n_i \ln(T_{1i})}{\sum_i n_i}$$

where $n_i$ is the mole of proton corresponding to the ith component with $T_1$ relaxation time in the $T_1$ distribution spectrum. With mole fraction expression, Equation 7 becomes:

$$\ln(T_{1LM}) = \sum_i f_i \ln(T_{1i}), \quad (8)$$

where $f_i$ is the mole fraction, $$\frac{n_i}{\sum_i n_i}.$$

For liquid samples, from Equations 3, 6, and 8, the log-mean of $T_1$ is:

$$\ln(T_{1LM}) \propto \frac{-1}{RT} \sum_i f_i E_{ai}. \quad (9)$$

For solid samples, from Equations 4, 6, and 8, the log-mean of $T_1$ is:

$$\ln(T_{1LM}) \propto \frac{1}{RT} \sum_i f_i E_{ai}. \quad (10)$$

In addition to $T_1$, $T_2$, and $T_1/T_2$, diffusion constants (D) of the components in a fluid may also provide a convenient parameter to monitor the wax formation or disappearance. The use of NMR to determine diffusion constants is well known to one skilled in the art, see e.g., U.S. Pat. Nos. 7,053,611 and 7,253,618, which are incorporated herein by reference in their entireties. For example, a conventional CPMG pulse sequence that is used to determine $T_2$ may be modified to provide diffusion measurements. In one example, a series of CPMG measurements may be obtained using different echo spacings (delay times between the 180 degree pulses in the CPMG pulse sequence) to encode the diffusion effects in the NMR signals. The diffusion effects arising from different echo spacings are then analyzed from the signals to provide estimates of the diffusion constants. Again, such diffusion constants may be used directly to monitor wax formation or disappearance. However it is more convenient to use these diffusion constants as a mean (particularly, logarithmic mean) for the monitoring.

In accordance with embodiments of the invention, NMR measurements are performed at several temperatures, and the NMR parameters thus obtained are then analyzed as a function of temperature to reveal the wax appearance temperature. Note that the obtained NMR parameters may be analyzed by themselves or in combination of two or more parameters (e.g., analyzed as a correlation of two or more parameters).

Figure 3:
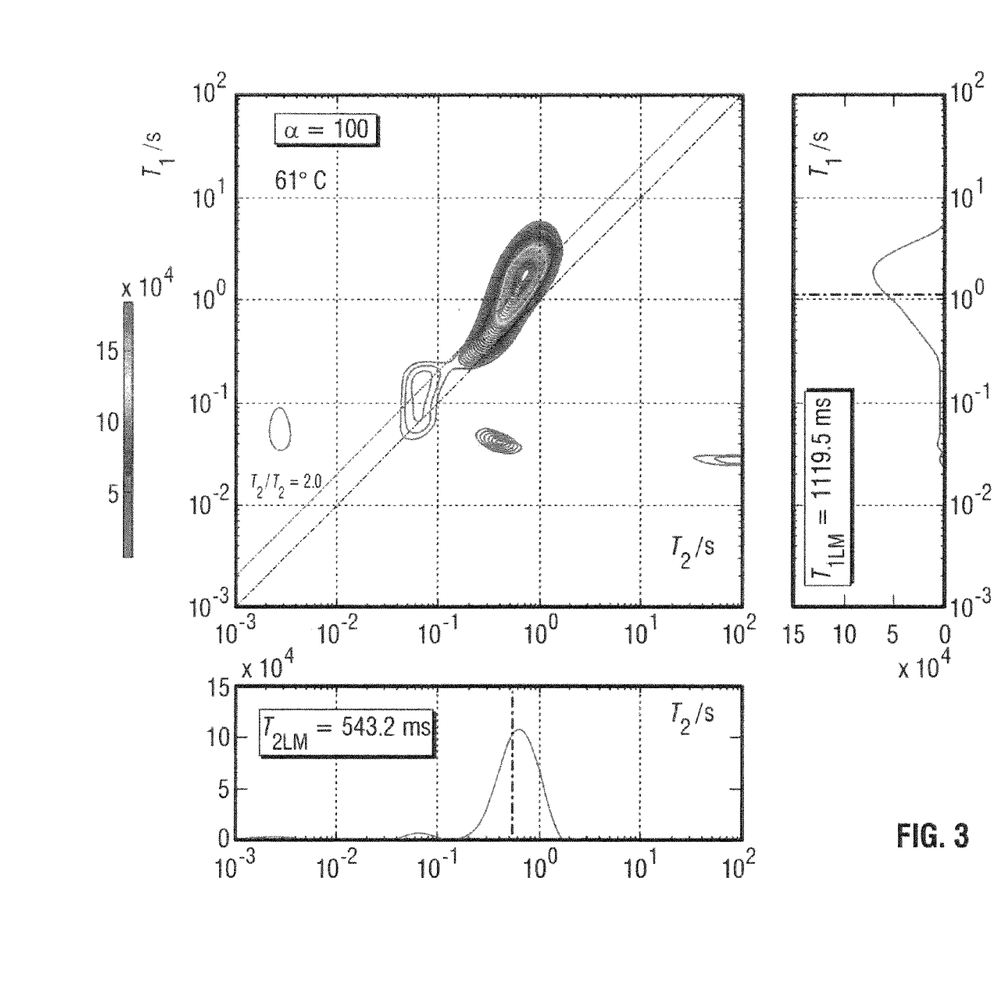
FIG. 3 shows $T_1$ and $T_2$ correlation of NMR results of a live fluid sample at 61° C. in accordance with one embodiment of the invention.
Figure 4:
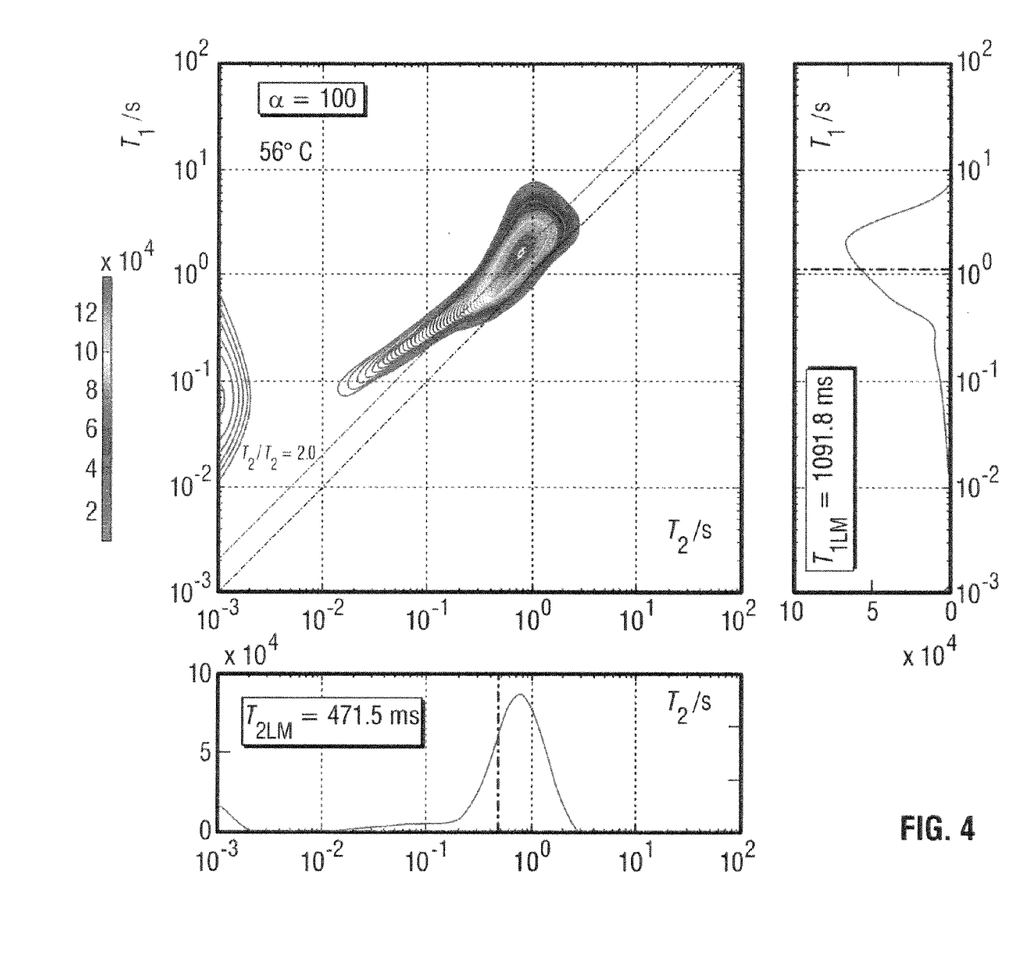
FIG. 4 shows $T_1$ and $T_2$ correlation of NMR results of a live fluid sample at 56° C. in accordance with one embodiment of the invention.
Figure 5:
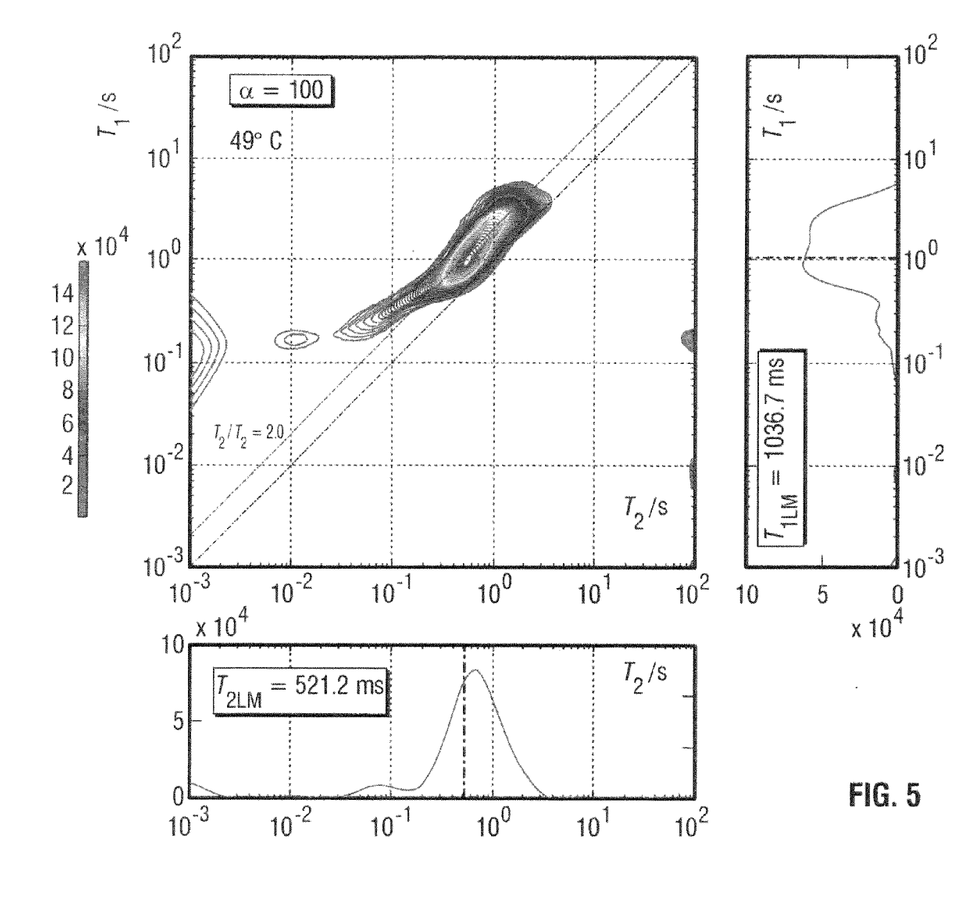
FIG. 5 shows $T_1$ and $T_2$ correlation of NMR results of a live fluid sample at 49° C. in accordance with one embodiment of the invention.

FIGS. 3-5 show examples of $T_1$-$T_2$ correlation graphs of NMR results obtained at 61° C., 56° C., and 49° C., respectively, from a live oil sample. On the sides of these graphs, projections of the $T_1$, $T_2$ distributions in the $T_1$ and $T_2$ axis are also shown.

As the temperatures are decreased from 61° C. (FIG. 3) to 56° C. (FIG. 4), both $T_1$ and $T_2$ decrease. At 49° C. (FIG. 5), $T_1$ continues to decrease, while $T_2$ increases. At this temperature the wax molecules precipitated and the solution became de-waxed, leading to an increase in $T_2$ value. These results are summarized in Table 1.

It is clear from the results shown in Table 1 that the $T_{2LM}$ time is significantly reduced at 56° C. As a result, the $T_{1LM}/T_{2LM}$ ratio is markedly increased. These results suggest that the wax appearance temperature for this particular sample is around 56° C. Similar results can also be obtained from diffusion measurements (not shown).

TABLE 1

| Temperature (° C.) | $T_{1LM}$ (ms) | $T_{2LM}$ (ms) | $T_{1LM}/T_{2LM}$ |
|---|---|---|---|
| 61 | 1119.5 | 543.2 | 2.06 |
| 56 | 1091.8 | 471.5 | 2.32 |
| 49 | 1036.7 | 521.2 | 1.99 |

Table 1 shows three NMR parameters ($T_{1LM}$, $T_{2LM}$, and $T_{1LM}/T_{2LM}$). It is apparent that both $T_{2LM}$ and $T_{1LM}/T_{2LM}$ show significant changes when wax forms, whereas the changes in $T_{1LM}$ are not as apparent. Thus, either $T_{2LM}$ or $T_{1LM}/T_{2LM}$ may be conveniently used to monitor the wax formation of this sample.

Figure 6:
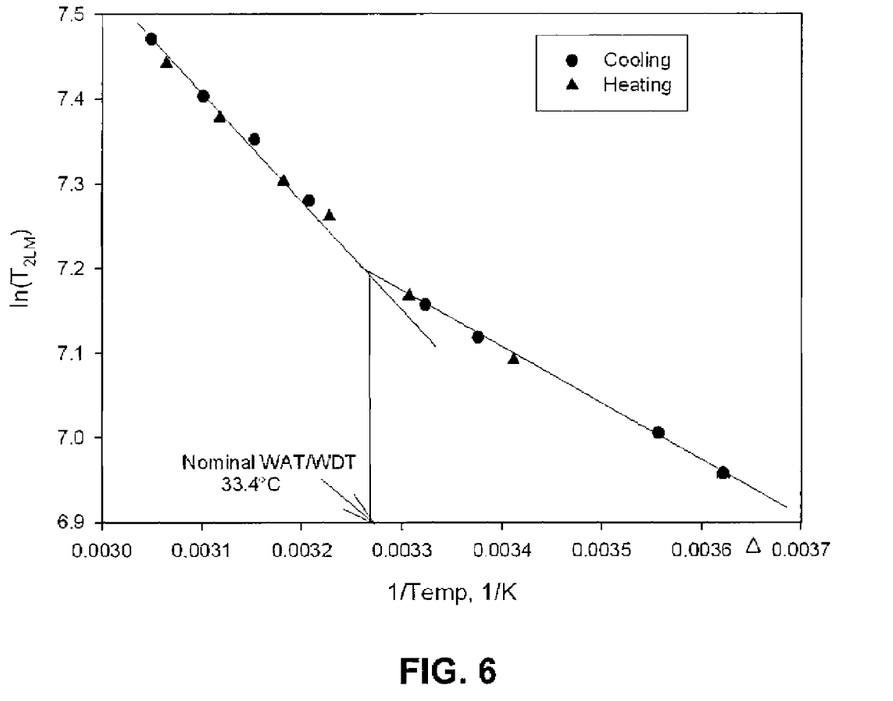
FIG. 6 shows $\ln(T_{2LM})$ and 1/T correlation of NMR results of a fluid of 20 percent paraffin wax and dodecane mixture in accordance with one embodiment of the invention.

FIG. 6 shows results of $T_2$ logarithmic means as a function of temperature change as detected by NMR methods of the invention. It is clear from this $\ln(T_{2LM})$ v. 1/K graph that this sample (20 percent paraffin wax in dodecane) exhibits two behavior regimes, which manifest themselves as two linear dependence regions. In the high temperature range (i.e., before wax formation), the natural log of $T_{2LM}$ ($\ln(T_{2LM})$) shows a linear dependence on 1/K with a steeper slope than that in the lower temperature (when wax has formed). The interception of these two lines suggests a transition (beginning of wax formation) occurred at a temperature (Nominal WAT/WDT) around 33.4° C. Note that these data points are obtained with both heating and cooling processes. The fact that these data points fall on the same lines, regardless of heating or cooling processes, indicates that the methods of the invention can detect the formation and disappearance of wax very precisely such that no "lag" is detected.

Figure 7:
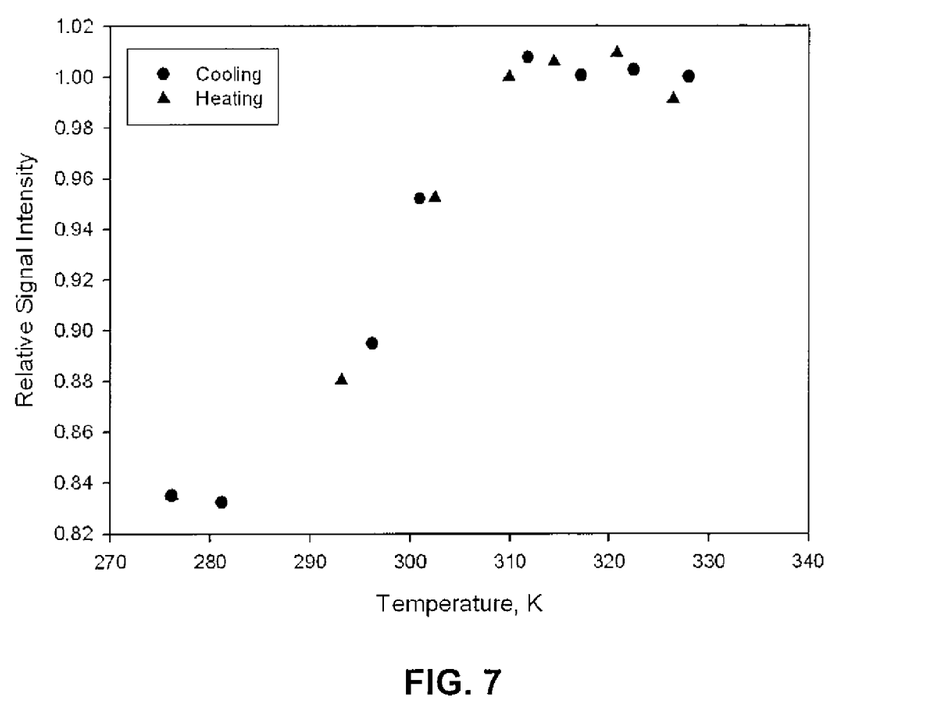
FIG. 7 shows relative NMR signal intensities, as compared to the signal intensities at the initial highest temperature, as a function of temperature (T) of a fluid sample of 20 percent paraffin wax and dodecane mixture in accordance with one embodiment of the invention.

FIG. 7 shows signal intensity changes as the temperatures are increased and lowered. Note that the heating and cooling processes produce almost superimposable transition curves in both directions, also suggesting that the methods of the invention detect the formation and disappearance of wax very precisely such that no "lag" is detected.

Figure 8:
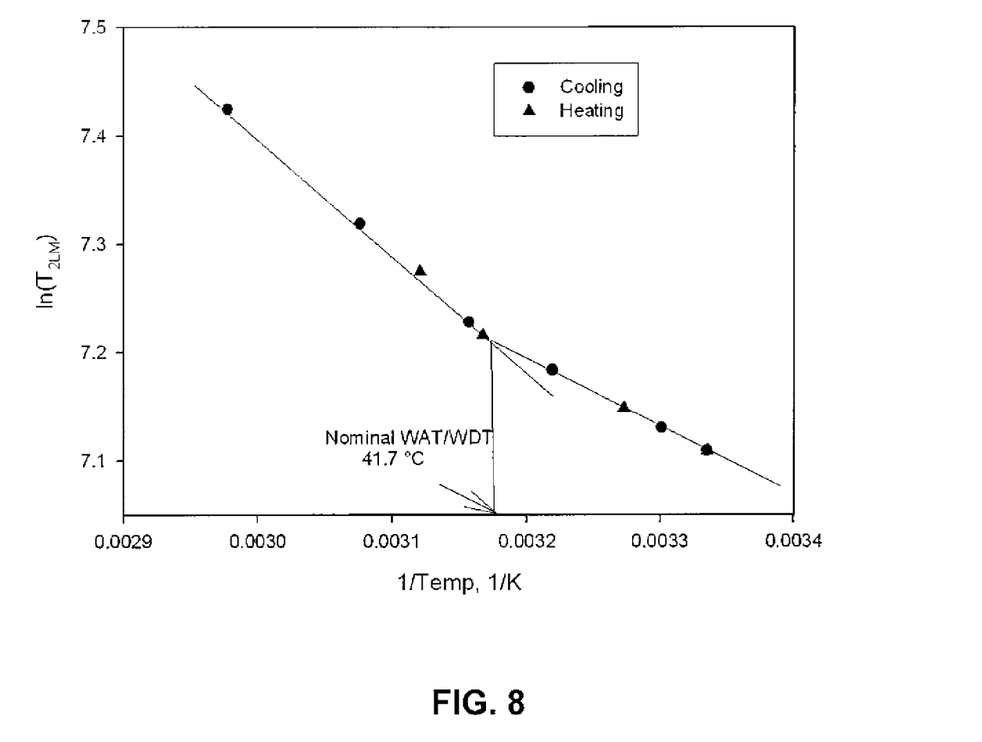
FIG. 8 shows $\ln(T_{2LM})$ and 1/T correlation of NMR results of a fluid of 30 percent paraffin wax and dodecane mixture in accordance with one embodiment of the invention.
Figure 9:
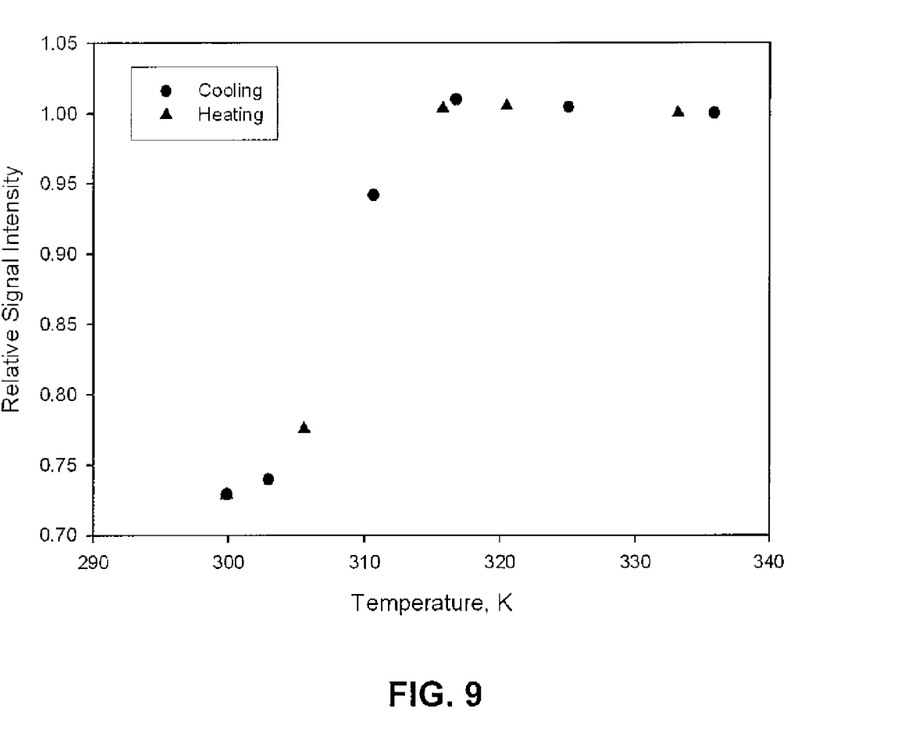
FIG. 9 shows relative NMR signal intensities, as compared to the signal intensities at the initial highest temperature, as a function of temperature (T) of a fluid sample of 30 percent paraffin wax and dodecane mixture in accordance with one embodiment of the invention.

FIG. 8 and FIG. 9 show results similar to those shown in FIGS. 6 and 7, but with a different sample—30 percent paraffin wax in dodecane. The wax formation temperature for this sample is around 41.7° C., as shown in FIG. 8. Again, the fact that the data points from cooling, and heating processes are superimposable suggests that the methods of the invention are very sensitive and can detect either the formation or disappearance of wax without any lag.

The methods of the present invention are more sensitive than conventional methods because the NMR methods detect phase transitions at the molecular level. In contrast, conventional methods typically rely on macroscopic (aggregate) behavior changes, which are less sensitive and will have lags because a sufficient number of the molecules must have undergone the phase transition before the methods can detect the "aggregate" changes. Table 2 shows the wax appearance temperatures of two samples (dodecane (C12) containing 20 percent paraffin wax and dodecane (C12) containing 30 percent paraffin wax) as detected by various methods, including differential scanning calorimetry (DSC), viscometry, visual inspection, pour point, and the NMR methods of the present invention. It is apparent that the NMR methods in accordance with embodiments of the invention are capable of detecting wax formation before (i.e., at higher temperatures) other methods can. The paraffin wax used in this case was Product No. 32, 721-2 offered by Sigma-Aldrich Canada Limited of Oakville, Ontario.

TABLE 2

| | Wax Appearance Temperature in ° C. | | | | |
|---|---|---|---|---|---|
| Composition | DSC | Viscometry | Visual | Pour Point | NMR |
| C12 + 20% Wax | 32.7 | 32.7 | 33.0 | 30 | 33.4 |
| C12 + 30% Wax | 38.1 | 36.8 | 38.0 | 35 | 41.7 |

Advantages of embodiments of the invention may include one or more of the following. Methods of the invention are more sensitive than conventional methods for monitoring wax formation or disappearance in a fluid. These methods make possible more accurate determination of the wax formation temperature, which can be more reliably used to predict potential problems in transferring a fluid in a pipe. Methods of the invention can be performed in a laboratory, on a pipeline, or in a wellbore. Apparatus for performing the methods of the invention can be readily modified from existing NMR devices.

While the invention has been described with respect to a limited number of embodiments, those skilled in the alt, having benefit of this disclosure, will appreciate that other embodiments can be devised which do not depart from the scope of the invention as disclosed herein. For example, a method of the invention may be performed in a laboratory or in a downhole environment. In addition, an apparatus of the invention for performing such methods may be a laboratory device, a module adapted to be attached to a pipeline, or a module on a downhole tool. Accordingly, the scope of the invention should be limited only by the attached claims.

What is claimed is:

1. A method for determining the wax appearance temperature of a fluid comprising:
    obtaining nuclear magnetic resonance (NMR) measurements of the fluid at a plurality of fluid temperatures;
    deriving an NMR parameter from each of the NMR measurements; and
    determining the wax appearance temperature of the fluid by analyzing the NMR parameter as a function of fluid temperature.

2. The method of claim 1, wherein the NMR parameter is one selected from the group consisting of $T_1$, a logarithmic mean of $T_1$ distribution, $T_2$, a logarithmic mean of $T_2$ distribution, $T_1/T_2$, diffusion constant (D), a logarithmic mean of diffusion constants, and NMR signal intensity.

3. The method of claim 1, wherein the NMR parameter is a logarithmic mean of $T_2$ or $T_1/T_2$.

4. The method of claim 1, wherein the NMR parameter is a diffusion constant or a logarithmic mean of diffusion constant distribution.

5. The method of claim 1, wherein the NMR parameter is NMR signal intensity.

6. A nuclear magnetic resonance (NMR) apparatus that detects wax appearance in a fluid, comprising:
    a sample cell configured for holding a fluid while NMR measurements are performed at a plurality of temperatures;
    a temperature measuring device disposed proximate the sample cell;
    a magnet configured for polarizing molecules within the fluid in the sample cell;
    at least one radiofrequency (RF) coil configured for generating pulses of magnetic field and configured for detecting NMR signals; and
    circuitry configured for controlling and measuring the temperature of the fluid in the sample cell and configured for obtaining NMR measurements.

7. The NMR apparatus of claim 6, wherein the sample cell has an inlet and an outlet such that it measures the fluid flowing therethrough.

8. The NMR apparatus of claim 6, further comprising a thermocouple disposed ill the sample cell that measures the temperature of the fluid therein.

9. Tile NMR apparatus of claim 6, wherein tile apparatus is configured to be used on a pipeline.

10. The NMR apparatus of claim 6, wherein the apparatus is configured to be used on a downhole tool.

* * * * *